(12) United States Patent
Radisch, Jr. et al.

(10) Patent No.: US 8,043,311 B2
(45) Date of Patent: Oct. 25, 2011

(54) MEDICAL DEVICE SYSTEMS

(75) Inventors: Herbert R. Radisch, Jr., San Diego, CA (US); Fuh-Sheng Chen, San Diego, CA (US); Show-Mean Wu, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2217 days.

(21) Appl. No.: 10/744,507

(22) Filed: Dec. 22, 2003

(65) Prior Publication Data
US 2005/0149102 A1   Jul. 7, 2005

(51) Int. Cl.
*A61M 29/00* (2006.01)
*A61F 2/06* (2006.01)

(52) U.S. Cl. ..................... 606/159; 623/1.11

(58) Field of Classification Search ............ 606/159, 606/170, 191, 194, 198; 604/103.01, 500, 604/501, 509, 96; 623/1.11
See application file for complete search history.

(56) References Cited

U.S. PATENT DOCUMENTS

| | | |
|---|---|---|
| 4,273,128 A | 6/1981 | Lary |
| 4,781,186 A | 11/1988 | Simpson et al. |
| 4,887,613 A | 12/1989 | Farr et al. |
| 4,896,669 A | 1/1990 | Bhate et al. |
| 4,909,781 A | 3/1990 | Husted |
| 5,030,201 A | 7/1991 | Palestrant |
| 5,053,044 A | 10/1991 | Mueller et al. |
| 5,074,871 A | 12/1991 | Groshong |
| 5,156,610 A | 10/1992 | Reger |
| 5,195,969 A | 3/1993 | Wang et al. |
| 5,209,799 A | 5/1993 | Vigil |
| 5,270,086 A | 12/1993 | Hamlin |
| 5,320,634 A * | 6/1994 | Vigil et al. ............ 606/159 |
| 5,336,234 A | 8/1994 | Vigil et al. |
| 5,728,123 A | 3/1998 | Lemelson et al. |
| 5,792,158 A | 8/1998 | Lary |
| 5,797,877 A | 8/1998 | Hamilton et al. |
| 5,797,935 A | 8/1998 | Barath |
| 6,027,514 A | 2/2000 | Stine et al. |
| 6,096,054 A | 8/2000 | Wyzgala et al. |
| 6,102,904 A * | 8/2000 | Vigil et al. ............ 604/500 |
| 6,258,108 B1 | 7/2001 | Lary |
| 6,416,526 B1 | 7/2002 | Wyzgala et al. |
| 6,428,539 B1 | 8/2002 | Baxter et al. |
| 6,632,231 B2 | 10/2003 | Radisch, Jr. |
| 7,252,650 B1 * | 8/2007 | Andrews et al. ........ 604/103.06 |
| 2002/0165523 A1 | 11/2002 | Chin et al. |
| 2003/0163157 A1 | 8/2003 | McMorrow et al. |
| 2004/0087899 A1 | 5/2004 | Weber |

* cited by examiner

*Primary Examiner* — Vy Q Bui
(74) *Attorney, Agent, or Firm* — Seager Tufte Wickhem LLC

(57) ABSTRACT

Medical device systems and related methods are disclosed.

50 Claims, 7 Drawing Sheets

MEDICAL DEVICE SYSTEMS

BACKGROUND

Balloon catheters can be used for a variety of medical procedures, such as, for example, to widen an occluded body vessel, as in angioplasty, to position a medical device, such as a stent or a graft, or to selectively block a passageway. A balloon catheter may include an inflatable and deflatable balloon positioned on a narrow catheter shaft. Prior to insertion and positioning of the balloon catheter within a patient's body, the balloon is folded around the shaft to reduce the radial profile of the medical device for easy and a traumatic insertion.

During use, for example, in angioplasty, the folded balloon can be positioned at a location in a vessel occluded by a stenosis by threading the balloon catheter over a guide wire placed in the body. The balloon is then inflated by introducing a fluid, such saline, into the interior of the balloon. Inflating the balloon can radially expand the stenosis so that the vessel can permit an increased rate of blood flow. After use, the balloon is deflated to its reduced radial profile and withdrawn from the body.

In some cases, it is desirable to incise at least a portion of the stenosis prior to radial expansion, thereby further increasing the blood flow rate.

SUMMARY

The invention relates to medical device systems, such as dilation balloon systems and balloon-catheter systems, methods of treating patients with medical device systems, and methods of making such medical device systems.

In one aspect, the invention features a system including an article and a scoring element carried by the article. The article includes a polymeric material and an additive material in the polymeric material. The article is configured to be carried by an expandable medical device and has an elongation at break that is at least about two times less than an elongation at break of the polymeric material.

In another aspect, the invention features a system including an article and a scoring element carried by the article. The article includes a polymeric material and an additive material in the polymeric material. The article is configured to be carried by an expandable medical device and has a tensile strength that is at least about two times greater than a tensile strength of the polymeric material.

In a further aspect, the invention features a system including an expandable medical device and an article carried by the expandable device. The article includes a polymeric material and an additive material in the polymeric material. The article has an elongation at break that is at least about two times less than an elongation at break of the polymeric material.

In one aspect, the invention features a system including an expandable medical device and an article carried by the expandable device. The article includes a polymeric material and an additive material in the polymeric material. The article has a tensile strength that is at least about two times greater than a tensile strength of the polymeric material.

In another aspect, the invention features a system including a pad, an additive material in the pad, and a scoring element carried by the pad. The pad is configured to be carried by an expandable medical device. The pad has an elongation at break that is at least about two times less than an elongation at break of the polymeric material.

In an additional aspect, the invention features a system that includes a pad, an additive material in the pad and a scoring element carried by the pad. The pad is configured to be carried by an expandable medical device, and the tensile strength of the pad is at least about two times greater than the tensile strength of the polymeric material.

In a further aspect, the invention features a system including an article having a surface and a bonding material on the surface of the article. The article includes a polymeric material and an additive material in the polymeric material. The article is configured to be carried by an expandable medical device and has an elongation at break that is at least about two times less than an elongation at break of the polymeric material.

In one aspect, the invention features a system including an article having a surface and a bonding material on the surface of the article. The article includes a polymeric material and an additive material in the polymeric material. The article is configured to be carried by an expandable medical device and has a tensile strength that is at least about two times greater than the tensile strength of the polymeric material.

In another aspect, the invention features a pad having a surface, an additive material in the pad, and a bonding material on the surface of the pad. The pad is configured to be carried by an expandable medical device and has an elongation at break that is at least about two times less than the elongation at break of the polymeric material.

In a further aspect, the invention features a pad having a surface, an additive material in the pad, and a bonding material on the surface of the pad. The pad is configured to be carried by an expandable medical device and has a tensile strength that is at least about two times greater than the tensile strength of the polymeric material.

In one aspect, the invention features a method of treating a lumen within a patient. The method includes inserting a system into the lumen and expanding the system. The system includes an article, a scoring element carried by the article, and an expandable device that carries the article. The article includes a polymeric material and an additive material in the polymeric material. The article has an elongation at break that is at least about two times less than the elongation at break of the polymeric material.

In another aspect, the invention features a method of treating a lumen within a patient. The method includes inserting a system into the lumen and expanding the system. The system includes an article, a scoring element carried by the article, and an expandable device that carries the article. The article includes a polymeric material and an additive material in the polymeric material. The article has a tensile strength that is at least about two times greater than the tensile strength of the polymeric material.

In a further aspect, the invention features a method of treating a lumen within a patient. The method includes inserting a system into the lumen and expanding the system. The system includes an expandable device and an article that is carried by the expandable medical device. The article includes a polymeric material and an additive material in the polymeric material. The article has an elongation at break that is at least about two times less than the elongation at break of the polymeric material.

In one aspect, the invention features a method of treating a lumen within a patient. The method includes inserting a system into the lumen and expanding the system. The system includes an expandable device and an article that is carried by the expandable medical device. The article includes a polymeric material and an additive material in the polymeric material. The article has a tensile strength that is at least about two times less than the tensile strength of the polymeric material.

In another aspect, the invention features a method of treating a lumen within a patient. The method includes inserting a system into the lumen and expanding the system. The system includes an expandable medical device, a pad, an additive material in the pad, and a scoring element carried by the pad. The pad has an elongation at break that is at least about two times less than the elongation at break of the polymeric material.

In a further aspect, the invention features a method of treating a lumen within a patient. The method includes inserting a system into the lumen and expanding the system. The system includes an expandable medical device, a pad, an additive material in the pad, and a scoring element carried by the pad. The pad has a tensile strength that is at least about two times greater than the tensile strength of the polymeric material.

In one aspect, the invention features a method of making a pad. The method includes combining an activator (e.g., a cross-linking agent) with a combination to form a mixture, and passing the mixture through an orifice and into a mold. The method also includes curing the mixture in the mold to form the pad. The combination includes a precursor (e.g., a monomer) and fibers.

Features and advantages of the invention are in the description, drawings and claims.

DETAILED DESCRIPTION

Figure 1:
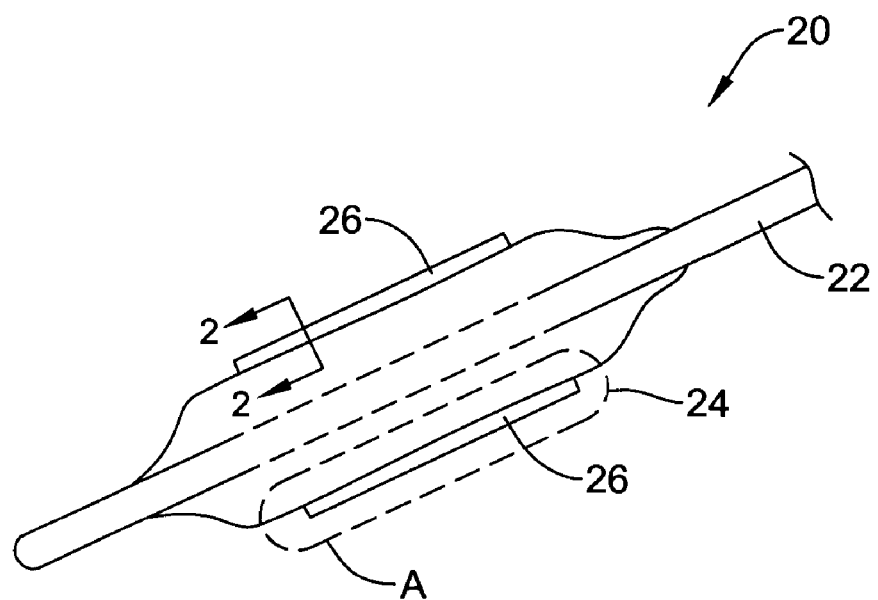
FIG. 1 is an illustration of an embodiment of a medical device system.
Figure 2:
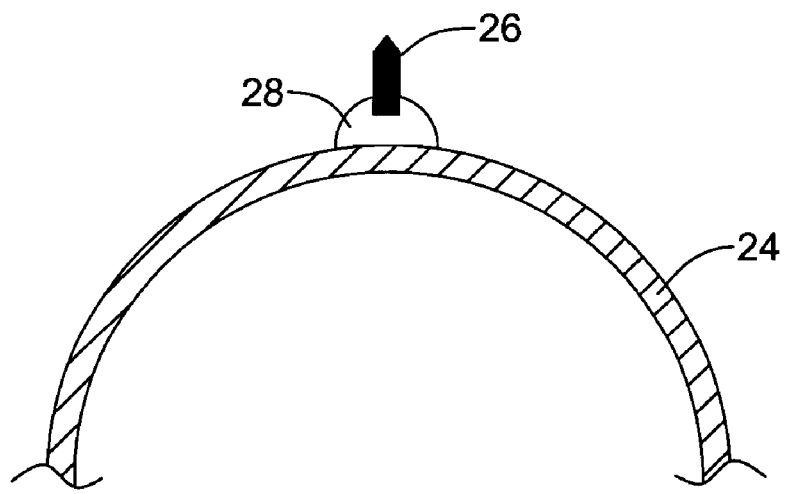
FIG. 2 is a cross sectional view of the medical device system of FIG. 1, taken along line 2-2.

Referring to FIGS. 1 and 2, a balloon catheter 20 for removing stenosis, such as plaque along coronary artery walls, includes a shaft 22, an inflatable balloon 24 attached to shaft 22, and one or more cutting elements 26 (here, two) attached to and carried by the inflatable balloon via pad 28 adhered to balloon 24 with a bonding material. The use of cutting elements 26 is by way of example only. In general, one or more scoring elements can be used. As referred to herein, when carried by a medical device, a scoring element is capable of scoring and/or cutting stenosis (e.g., plaque along artery walls). In some embodiments, a scoring element can, for example, be in the shape of a wire (e.g., a metal wire, a polymer wire).

Figure 3:
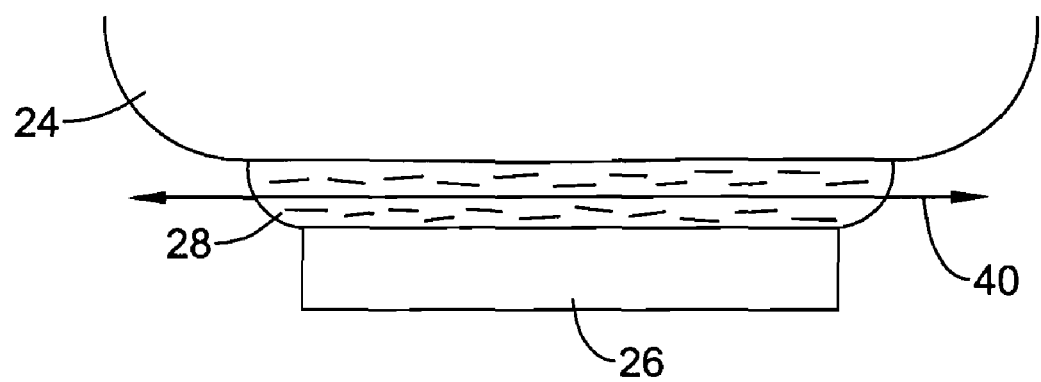
FIG. 3 is an expanded view of a portion of the medical device system labeled A in FIG. 1.

As shown in FIG. 3, pad 28 is formed of one or more polymeric materials that contain fibers that are substantially oriented along a longitudinal direction 40. For example, in some embodiments, the fibers can be oriented within the article such that at least about 50% (e.g., at least about 60%, at least about 70%) of the fibers are oriented within about 30 degrees of a longitudinal direction of the article.

Without wishing to be bound by theory, it is believed that including fibers in pad 28 can increase the stiffness of pad 28 along the direction in which the fibers are substantially oriented (e.g., the longitudinal direction of pad 28). It is believed that the increased stiffness of pad 28 can reduce the ability of pad 28 to grow in the direction in which the fibers are substantially oriented (e.g., reduce the ability of pad 28 to grow in the longitudinal direction of pad 28 as balloon 24 is expanded). It is further believed that the reduced ability of pad 28 to grow can reduce the likelihood of cutting element 26 separating from pad 28 and/or reduce the likelihood of pad 28 separating from balloon 24 (e.g., when balloon 24 is expanded). It is believed that the fibers have little or no effect on flexibility of pad 28 in directions in which the fibers are not substantially oriented, and that the fibers therefore have little or no effect on the overall flexibility of catheter 20 (e.g., the overall flexibility of catheter 20 when catheter 20 is being disposed in or moved in a body lumen).

In certain embodiments, pad 28 containing fibers has a relatively low elongation at break. For example, the elongation of break of pad 28 (which includes fibers) can be at least about two times less (e.g., at least about five times less, at least about 10 times less, at least about 100 times less) than the elongation of break of a pad made of the same polymeric material(s) but without fibers. In some embodiments, the elongation at break for pad 28 (including fibers) is at least about 50% (e.g., at least about 60%, at least about 70%). As referred to herein, elongation at break is measured using ASTM test procedure D638.

In some embodiments, pad 28 containing fibers has a relatively high tensile strength. For example, the tensile strength of pad 28 (which includes fibers) can be at least about two times greater (e.g., at least about 10 times greater, at least about 50 times greater) than the tensile strength of a pad made of the same polymeric material(s) but without fibers. In general, pad 28 (including fibers) has a tensile strength of at least about 3,000 psi (e.g., at least about 5,000 psi, at least about 7,500 psi). As referred to herein, tensile strength is measured using ASTM test procedure D638.

In certain embodiments, pad 28 contains at most about 10 weight percent (e.g., at most about seven weight percent, at most about five weight percent) fibers, and/or pad 28 contains at least about 90 weight percent (e.g., at least about 93 weight percent, at least about 95 weight percent) polymeric material (s).

In some embodiments, the fibers have an average aspect ratio of at least about 10 to 1 (e.g., at least about 20 to 1, at least about 50 to 1). As referred to herein, the average aspect ratio of a collection of fibers (e.g., the fibers contained in a pad) refers to the average length to width ratio of the collection of fibers.

The fibers contained in a pad can have a variety of different cross-sectional shapes (e.g., width shapes), such as, for example, circular, square, rectangular, octagonal, triangular, oval, and elliptical.

Generally, the fibers contained in pad 28 can be selected as desired. Typically, the fibers are selected to increase the stiffness of pad 28 and to reduce the likelihood of separation of cutting elements 26 from pad 28. Examples of fibers include boron fibers, silk fibers (e.g., natural silk fibers, synthetic silk fibers, spider silk fibers), carbon fibers (e.g., graphite fibers and PANEX® milled carbon fibers provided by Zoltek Companies, Inc., St. Louis, Mo.), polymer fibers (e.g., aramid fibers including Dacron® fibers and Kevlar® fibers, both provided by DuPont deNemours & Co., Wilmington, Del.), glass fibers (e.g., OC™ milled glass fibers provided by Owens Corning, Toledo, Ohio), and ceramic fibers. In some embodiments, the fibers in pad 28 can be formed of different materials.

In general, the polymeric material(s) in pad 28 can be selected as desired. Typically, the polymeric material is selected to be biocompatible with the subject in which catheter 20 is to be used. Examples of polymeric materials that can be used in pad 28 include urethanes (e.g., thermoplastic urethanes), silicones, natural rubbers, and elastomers. Combinations of polymeric materials can be used.

Examples of bonding materials that can be used to adhere pad 28 to balloon 24 include polyurethanes, cyanoacrylates, and adhesives, such as, for example, epoxies, aerobic adhesives, and acrylic adhesives. Combinations of bonding materials can be used.

In general, inflatable balloon 24 can have any of a variety of shapes or sizes. In certain embodiments, inflatable balloon 24 can be a coronary balloon, an aortic balloon, a peripheral balloon, a reperfusion balloon, an endoscopy balloon, a gastrointestinal balloon, a urological balloon or a neurological balloon. In some embodiments, balloon 24 has a diameter of at least 1.5 millimeters (e.g., at least about two millimeters, at least about three millimeters, at least about four millimeters, at least about five millimeters, at least about six millimeters) when inflated. As an example, balloon 24 can be a peripheral balloon having a diameter of at least about three millimeters (e.g., at least about five millimeters, at least about seven millimeters, at least about nine millimeters, at least about 12 millimeters) when inflated. As another example, balloon 24 can be a urological balloon having a diameter at least about four millimeters (e.g., at least about 10 millimeters, at least about 20 millimeters, at least about 30 millimeters, at least about 40 millimeters) when inflated. As a further example, balloon 24 can be a neurological balloon having a diameter at least about 1.5 millimeters (e.g., at least about two millimeters, at least about three millimeters, at least about four millimeters, at least about five millimeters).

In general, pad 28 can be prepared as desired. In certain embodiments, pad 28 can be prepared as follows. One or more precursors (e.g., one or more monomers) of the polymeric material(s) is/are degassed in a vacuum oven for at least about 15 minutes at a temperature of about 23.9° C. and a pressure of about 30 inches of Hg. One or more activators (e.g., one or more cross-linking agents) for the precursor(s) is/are added to the precursor. Prior to mixing, the fibers are added to the combination of precursor and activator. The weight of the fibers added is less than or equal to about 10 weight percent (wt %), (e.g., less than or equal to about 9 wt %, less than or equal to about 8 wt %, less than or equal to about 7 wt %, less than or equal to about 6%, less than or equal to about 5 wt %, less than or equal to about 4 wt %, less than or equal to about 3 wt %, less than or equal to about 2%, less than or equal to about 1%) of the total weight of the combination. The combination with the fibers is mixed together manually with a stirrer in a mixing cup for about 90 seconds. During mixing, the sides and bottom of the mixing cup are scraped with the stirrer to provide a well mixed combination. Alternatively or additionally, the combination with fibers can be mixed together automatedly with a mixing machine, such as the Keyence Mixer, model no. AR-250, available from Tomen America Inc., Charlotte, N.C.

After mixing the combination is degassed for about two minutes in the vacuum oven at a temperature of about 19.5° C. (room temperature) and a pressure of about 30 inches of Hg. This combination is passed through an orifice and into a mold. In some embodiments, the orifice is small enough (e.g., less than about 10 mils in diameter, less than about seven mils in diameter, less than about five mils in diameter) to substantially orient the fibers. An example of a device that includes a suitable orifice is a gun type applicator, such as the DG3 DispensGun® (EFD Inc., East Providence, R.I.) having a 25 gage or greater (e.g., 26 gage or greater, 27 gage or greater, 28 gage or greater, 29 gage or greater, 30 gage or greater) ejection tip. The combination is reacted in the mold to form the pad. Typically, the cutting element is inserted into the pad (e.g., into a slot formed in the combination), and the combination is then cured in an oven at a temperature of about 67° C. for a minimum of six hours and a maximum of 14 hours. Alternatively or additionally, the cutting element can be secured to the pad using an adhesive (e.g., by curing the combination to form the pad first, and then using the adhesive to secure the cutting element to the pad).

Examples of precursors include Conathane® RN-1570, Conathane® RN-1571, Conathane® RN-1558, Conathane® RN-1559, and Conathane® RN-560, available from Cytec Industries Inc., Coatings & Performance Chemicals, Olean, N.Y. Examples of activators include Tonox®, Tonox®22, and Tonox®LC, available from Crompton Corporation, Middlebury, Conn. As an example, the precursor can be Conathane® RN-1570, and the activator can be Tonox®LC. As another example, the precursor can be Conathane® RN-1570, and the activator can be Tonox®22. As a further example, the precursor can be Conathane® RN-1570, and the activator can be Tonox®.

Figure 4A:
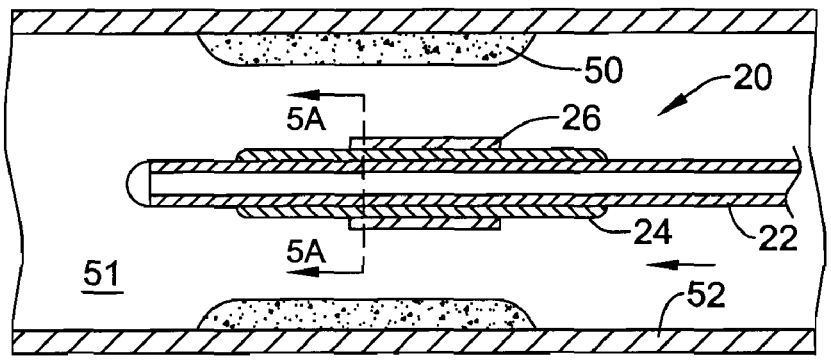
FIGS. 4A, 4B, and 4C illustrate an embodiment of a method of using the medical device system of FIG. 1.
Figure 4B:
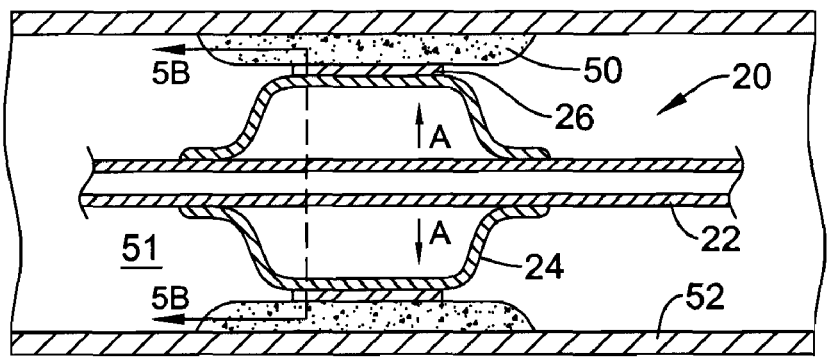
Figure 4C:
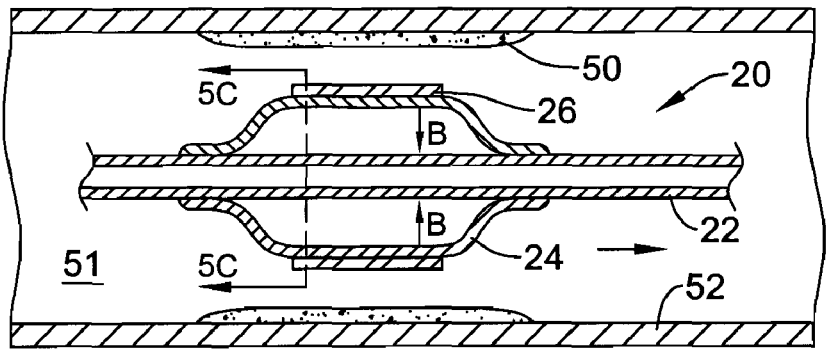
Figure 5A:
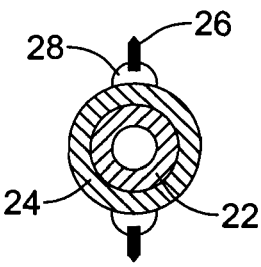
FIGS. 5A, 5B, and 5C are cross sectional view of the medical device system shown in FIGS. 4A, 4B, and 4C, respectively, taken along lines 5A-5A, 5B-5B, and 5C-5C, respectively.
Figure 5B:
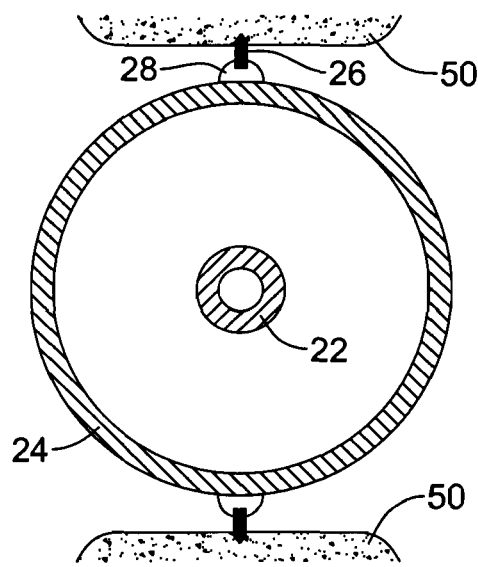
Figure 5C:
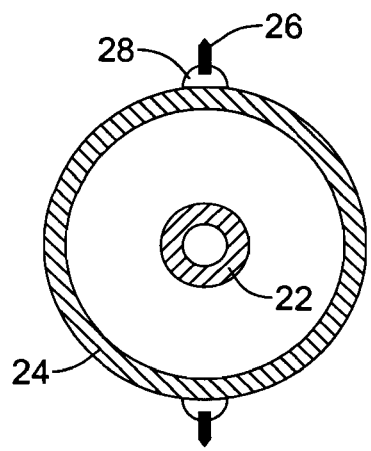

Referring to FIGS. 4A, 4B, and 4C, a method of using catheter 20 is shown. Catheter 20 is delivered to a target site 51, e.g., one having a calcified region 50, using conventional methods such as by treading catheter shaft 22 over an emplaced guide wire (not shown). Balloon 24 is unexpanded so that catheter 20 can easily navigate through the patient's body without causing trauma to vessel walls 52 (FIG. 5A). After catheter 20 is properly positioned, balloon 24 is radially expanded (arrows A shown in FIG. 4B), e.g., by introducing a fluid into the interior of the balloon through an inflation lumen (not shown) extending along catheter shaft 22. As balloon 24 is expanded, cutting elements 26 are advanced radially outer toward calcified region 50 until cutting elements 26 pierce and/or contact calcified region 50 (FIG. 5B). Catheter 20 can be moved (e.g. translated and/or rotated) to provide a desired cutting action to remove, at least in part, calcified region 50 from vessel wall 52. Subsequently, balloon 24 is deflated (arrows B shown in FIG. 4C) so that cutting elements 26 are withdrawn from the vessel wall 52 (FIG. 5C). Catheter 20 is then removed according to conventional methods.

In general, catheter 20 can be used to treat blocked or partially blocked lumens within a patient's body. For example, in certain embodiments, catheter 20 is used to treat blockages in coronary arteries. In some embodiments, catheter 20 is used to treat blockages in the urinary tract. In certain embodiments, catheter 20 is used to treat blockages in the gastrointestinal tract.

The following examples are illustrative and not intended to be limiting.

EXAMPLE I

A pad having polymeric material and fibers is formed using the following process. 3.5 grams of urethane (Conathane® RN-1570, manufactured by Cytec Industries Inc., Coatings & Performance Chemicals, Olean, N.Y.) are placed into a mixing cup. The cup including the urethane is transferred into a vacuum oven and degassed for at least 15 minutes at 23.9° C. and 30 inches of Hg. Then 0.5 gram of Tonox® (manufactured by Crompton Corporation, Middlebury, Conn.) and 0.4 gram or less of OC™ milled glass fibers (commercially available from Owens Corning, Toledo, Ohio) are added to the mixing cup. The combination of Conathane® RN-1570, Tonox®, and OC™ milled glass fibers is mixed together with a stirrer in the mixing cup for 90 seconds. While mixing, the bottom and sides of the mixing cup are scraped with the stirrer to ensure that all of the contents within the mixing cup are well mixed.

The mixing cup with the mixed combination of Conathane® RN-1570, Tonox®, and OC™ milled glass fibers is placed in a vacuum oven and degassed for two minutes at a temperature of 19.5° C. and a pressure of 30 inches of Hg. The mixed combination is loaded into a gun type applicator, model no. DG3 DispensGun® (commercially available from EFD Inc., East Providence, R.I.) having a 25 gage SmoothFlow® tapered tip, model no. 5125TT-B (commercially available from EFD Inc., East Providence, R.I.). The mixed combination is ejected from the gun type applicator onto a silicone mat to form multiple mounds of the mixed combination. Each mound is approximately 2 millimeters in diameter.

To cure the combination, the mat is transferred into an aluminum curing mold and placed into an oven set to 67° C. with a 2.6 pound aluminum weight positioned on top of the mold for at least about six hours. The mold is then removed from the oven and the pads are removed from the mat.

EXAMPLE II

A pad having polymeric material and fibers is formed using the following process. 3.5 grams of urethane (Conathane® RN-1571, manufactured by Cytec Industries Inc., Coatings & Performance Chemicals, Olean, N.Y.) are placed into a mixing cup. The cup including the urethane is placed into a vacuum oven and degassed for at least 15 minutes at 23.9° C. and 30 inches of Hg. Then 0.5 gram of Tonox® 22 (manufactured by Crompton Corporation, Middlebury, Conn.) and 0.4 gram or less of PANEX® milled carbon fibers (commercially available from Zoltek Companies, Inc., St. Louis, Mo.) are added to the mixing cup. The combination of Conathane® RN-1571, Tonox® 22, and PANEX® milled carbon fibers is mixed together with a Keyence Mixer, model no. AR-250, commercially available from Tomen America Inc., Charlotte, N.C. The total mixing time is 120 seconds. After mixing, the combination is defoamed (i.e., bubbles generated during the mixing process are removed) by activating the defoam setting on the mixer. The total defoam time is 60 seconds.

The mixing cup with the mixed combination of Conathane® RN-1571, Tonox® 22, and PANEX® milled carbon fibers is then placed in a vacuum oven and degassed for two minutes at a temperature of 19.5° C. and a pressure of 30 inches of Hg. The mixed combination is loaded into a gun type applicator, model no. DG3 DispensGun® (commercially available from EFD Inc., East Providence, R.I.) having a 25 gage SmoothFlow® tapered tip, model no. 5125TT-B (commercially available from EFD Inc., East Providence, R.I.). The mixed combination is ejected from the gun type applicator onto a silicone mat to form multiple mounds of the mixed combination. Each mound is approximately 2 millimeters in diameter.

To cure the combination, the mat is transferred into an aluminum curing mold and then placed into an oven set to 67° C. with a 2.6 pound aluminum weight positioned on top of the mold for eight hours. The mold is then removed from the oven and the pads are removed from the mat.

EXAMPLE III

A pad made from polymeric material and fibers and having a blade attached is formed using the following process. 3.5 grams of urethane (Conathane® RN-1558, manufactured by Cytec Industries Inc., Coatings & Performance Chemicals, Olean, N.Y.) are placed into a mixing cup. The cup including the urethane is placed into a vacuum oven and degassed for at least 15 minutes at 23.9° C. and 30 inches of Hg. Then 0.5 gram of Tonox® LC (manufactured by Crompton Corporation, Middlebury, Conn.) and 0.4 gram or less of milled Kevlar® fibers (commercially available from DuPont deNemours & Co., Wilmington, Del.) are added to the mixing cup. The combination of Conathane® RN-1558, Tonox® LC, and Kevlar® milled fibers is mixed together with a Keyence Mixer, model no. AR-250, commercially available from Tomen America Inc., Charlotte, N.C. The total mixing time is 120 seconds. After mixing, the combination is defoamed by activating the defoam setting on the mixer. The total defoaming time is 60 seconds.

The mixing cup with the mixed combination of Conathane® RN-1558, Tonox® LC, and Kevlar® milled fibers is then placed in a vacuum oven and degassed for two minutes at a temperature of 19.5° C. and a pressure of 30 inches of Hg. The mixed combination is loaded into a gun type applicator, model no. DG3 DispensGun® (commercially available from EFD Inc., East Providence, R.I.) having a 25 gage Smooth Flow® tapered tip, model no. 5125TT-B (commercially available from EFD Inc., East Providence, R.I.). The mixed combination is ejected from the gun type applicator onto a silicone mat containing blades that have a length of 0.310" (part no. 1844, available from Boston Scientific, San Diego, Calif.) and a length of 0.510" (part no. 1845, available from Boston Scientific, San Diego, Calif.). The blades are partially disposed within slits cut in the silicone mat (i.e., only a portion of the blade is visible, the remainder of the blade is surrounded by the mat). Each blade in the silicone mat is coated with a layer of the mixed combination to form a pad 2 millimeters in width and 2 millimeters in height. The mixed combination is applied along the length of the blade such that the entire portion of the blade extending from the mat is coated with an even layer of the mixed combination. Prior to ejection of the mixed combination, the mat with blades is degassed on a hotplate at 67° C. for five minutes.

To cure the combination to form the pads with blades, the mat is transferred into an aluminum curing mold and placed into an oven set to 67° C. with a 2.6 pound aluminum weight positioned on top of the lid of the mold for 10 hours. The mold is then removed from the oven and the pads with blades attached are removed from the mat.

EXAMPLE IV

A pad made from polymeric material and fibers and having a blade attached is formed using the following process. 35 grams of urethane (Conathane® RN-1550, manufactured by Cytec Industries Inc., Coatings & Performance Chemicals, Olean, N.Y.) are placed into a mixing cup. The cup including the urethane is placed into a vacuum oven and degassed for at least 15 minutes at 23.9° C. and 30 inches of Hg. Then five grams of Tonox® (manufactured by Crompton Corporation, Middlebury, Conn.) and four grams or less of milled OC™ milled glass fibers (commercially available from Owens Corning, Toledo, Ohio) are added to the mixing cup. The combination of Conathane® RN-1550, Tonox®, and OC™ milled glass fibers is mixed together with a Keyence Mixer, model no. AR-250, commercially available from Tomen America Inc., Charlotte, N.C. The total mixing time is 120 seconds. After mixing, the combination is defoamed by activating the defoam setting on the mixer. The total defoam time is 60 seconds.

The mixing cup with the mixed combination of Conathane® RN-1550, Tonox®, and OC™ milled glass fibers is then placed in a vacuum oven and degassed for two minutes at a temperature of 19.5° C. and a pressure of 30 inches of Hg. The mixed combination is loaded into the feed-zone of a BOY Liquid Silicon Injection (LSI) Molding Machine, model 80A, available from BOY Machinery Inc., Exton, Pa. The mixed combination is ejected from the LSI onto a silicone mat containing blades that have a length of 0.310" (part no. 1844, available from Boston Scientific, San Diego, Calif.) and a length of 0.510" (part no. 1845, available from Boston Scientific, San Diego, Calif.). The blades are partially disposed within slits cut in the silicone mat (i.e., only a portion of the blade is visible, the remainder of the blade is surrounded by the mat). Each blade in the silicone mat is coated with a layer of the mixed combination by the BOY LSI Molding Machine. Prior to injection of the mixed combination, the mat with blades is degassed on a hotplate at 67° C. for five minutes.

After injection, the silicone mat is transferred into an aluminum curing mold and placed into an oven set to 67° C. with a 2.6 pound aluminum weight positioned on top of the lid of the mold for one hour. The silicone mat with partially cured pads is then removed from the aluminum mold. The mat and pads are heated for an additional 10 hours at 67° C. outside of the aluminum mold to completely cure the pads. Subsequent to curing, the pads with blades attached are removed from the silicone mat.

While certain embodiments have been described, other embodiments are also possible.

As an example, while pads have been described that contain fibers that are substantially oriented, in some embodiments, the fibers can have different orientations (e.g., randomly oriented).

As a further example, while article containing fibers have been described, in certain embodiments, the fibers can be replaced with one or more woven fabrics (e.g., one or more polyester woven fabrics). The fibers in the woven fabric can be oriented in one of two directions, e.g., horizontal fibers and vertical fibers. It is believed that this can increase the resistance to elongation of the article (e.g., pad) along the lengths of the horizontal fibers and the vertical fibers. In some embodiments, an article (e.g., a pad) contains fibers and one or more woven fabrics.

As an additional example, in some embodiments, an article (e.g., a pad) includes a plurality of fibers. A first portion of the plurality of fibers are substantially oriented in a first direction, a second portion of the plurality of fibers are substantially oriented in a second direction, and a third portion of the plurality of fibers are substantially oriented in a third direction. That is, some of the fibers in the plurality are substantially oriented in the first direction, other fibers in the plurality are substantially oriented in the second direction, and the remaining fibers in the plurality are substantially oriented in the third direction. In some embodiments, the plurality of fibers can be substantially oriented in at least about four different directions.

Figure 6:
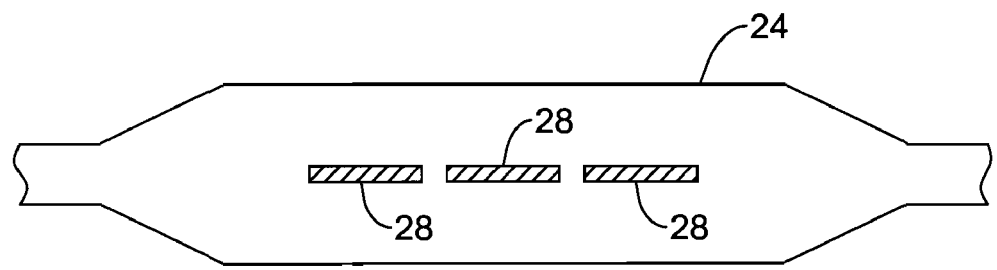
FIG. 6 is a plan view of an embodiment of a medical device system.
Figure 7:
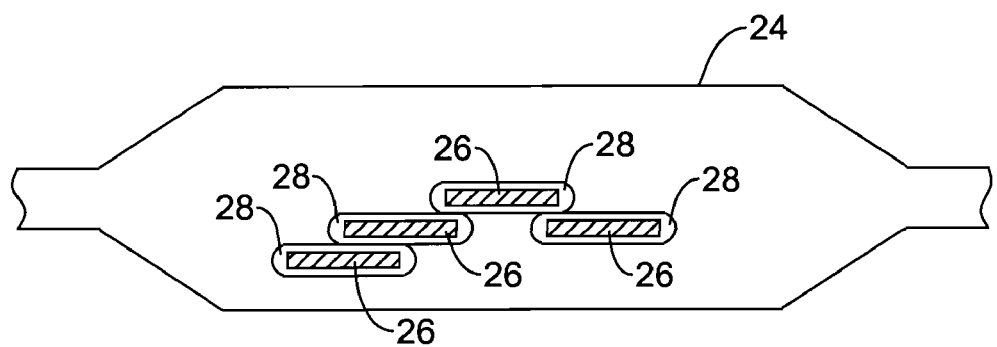
FIG. 7 is a plan view of an embodiment of a medical device system.

As an example, while an inflatable balloon has been having two pads, an inflatable balloon can have more or less than two pads (e.g., one pad, three pads, four pads, five pads, six pads, seven pads, eight pads). The pads can be equally and/or unequally spaced around the circumference of the balloon. For example, for a balloon having six pads spaced about the balloon's circumference, the pads can be formed at 2 o'clock, 3 o'clock, 4 o'clock, 8 o'clock, 9 o'clock and 10 o'clock. A pad located at 3 o'clock is equally spaced with the pads at 2 o'clock and 4 o'clock; but for example, the pad at 4 o'clock is unequally spaced with the pad at 3 o'clock and 8 o'clock. In addition, the pads can by symmetrically or asymmetrically positioned around the circumference and/or length of the balloon. Referring to FIG. 6, multiple pads (e.g., two three, four, five or more) can be arranged collinearly (e.g., spaced and end-to end) along balloon 24. Alternatively or additionally, multiple pads can be arranged side-by-side, i.e., adjacent to each other. In some embodiments, multiple pads 28 with cutting elements 26 can be adjacent to each other and overlapping along the longitudinal direction of balloon 24 (FIG. 7).

Figure 8:
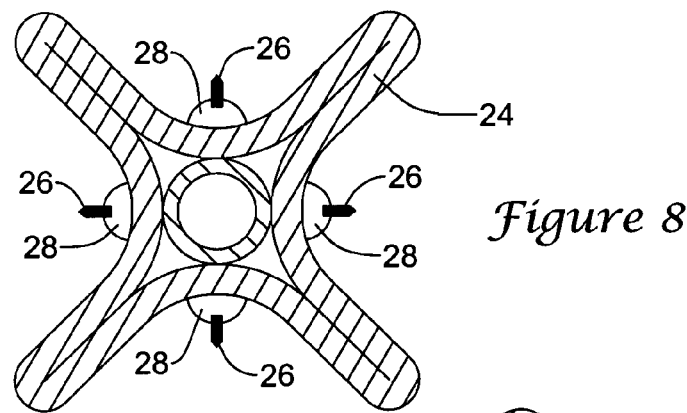
FIG. 8 is a cross sectional view of an embodiment of a non-expanded medical device system.
Figure 9:
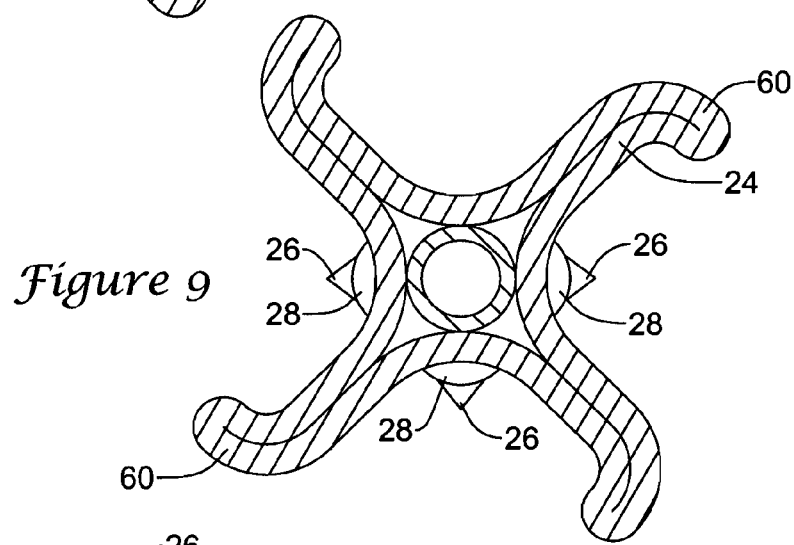
FIG. 9 is a cross sectional view of an embodiment of a non-expanded medical device system.

As an additional example, in some embodiments, balloon 24 can be folded (FIG. 8) using the methods described in Vigil U.S. Pat. Nos. 5,209,799 and 5,336,234, both hereby incorporated by reference in their entirety. In certain embodiments, referring to FIG. 9, relatively compliant areas of balloon 24, e.g., flaps 60, can be folded over cutting elements 26 to protect a patient's body lumen from cutting elements 26. Folding can be performed by engaging, e.g., grasping, flaps 60 with a chuck, and rotating the chuck. Folding can be performed during heat treatment of balloon 24, as described in Vigil U.S. Pat. No. 5,209,799. Other methods of folding balloon 24 are described in U.S. Ser. No. 10/087,303 filed on Feb. 28, 2002 and published on Aug. 28, 2003 as U.S. Publication No. 2003163157.

As a further example, in some embodiments, a balloon and/or a shaft can have a wall having a plurality of layers formed of polymers. Multilayer devices are described in Hamlin U.S. Pat. No. 5,270,086; Wang U.S. Pat. No. 5,195,969; Hamilton U.S. Pat. No. 5,797,877; and U.S. Ser. No. 09/798,749, entitled "Multilayer Medical Device," filed on Mar. 2, 2001, and published on Nov. 7, 2002 as U.S. Publication No. 20020165523, all hereby incorporated by reference in their entirety. The layers can be selected to provide the balloon and/or the shaft with desired properties. Different combinations of layering (e.g., materials, sequences, and/or thickness) can be used, as described in U.S. Ser. No. 09/798, 749.

As an additional example, while an article that carries a cutting or scoring element has been described as a pad, any article type or portion of an expandable medical device can carry a cutting element. Generally, such an article includes one or more polymeric material and fibers.

Figure 10:
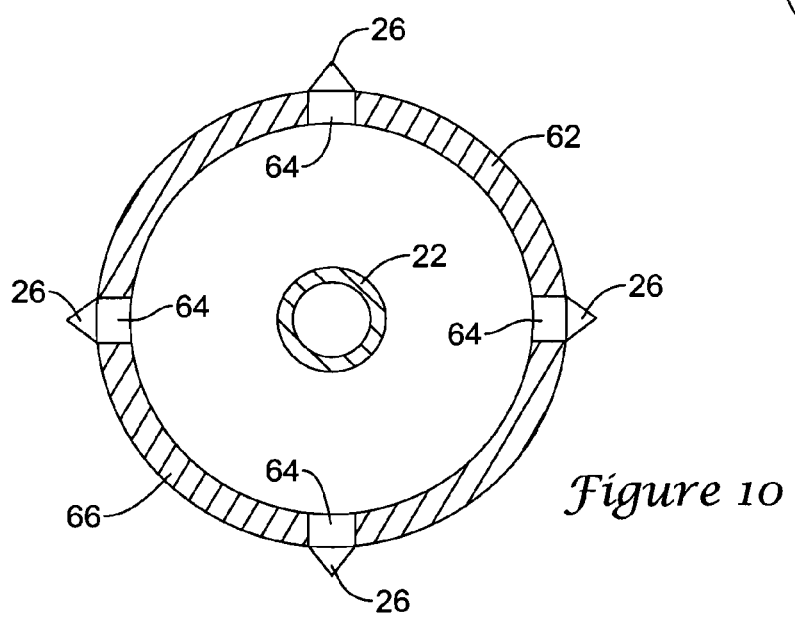
FIG. 10 is a cross sectional view of an embodiment of a medical device system.

As another example, referring to FIG. 10, one or more striped portions 64 of balloon 66 can be co-extruded to include polymeric material and fibers. As a result, striped portions 64 have increased resistance to elongation as compared to portions of balloon 66 containing solely polymeric material (e.g., elongation at break of striped portions 64 is at least about two times less than the elongation at break of the polymeric material and/or tensile strength of striped portions 64 is at least two times greater than the tensile strength of the polymeric material). Cutting elements 26 are attached to balloon 66 over striped portions 64. During expansion of balloon 66, striped portions 64 experience less elongation along the direction of fiber orientation. As a result, mechanical stress between cutting elements 26 and balloon 24 is reduced, and attachment there between is enhanced.

Figure 11:
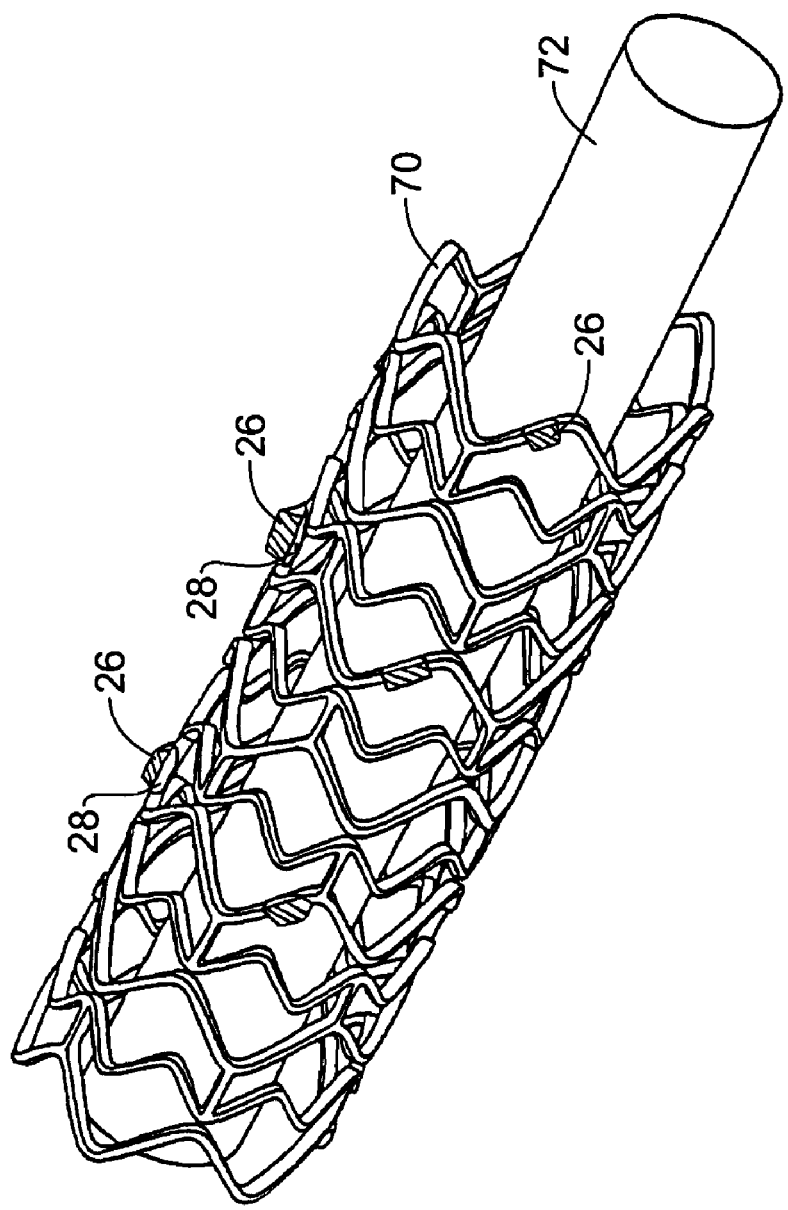
FIG. 11 is a plan view of an embodiment of a medical device system.

As an additional example, referring to FIG. 11, in some embodiments, one or more pads 28 including cutting elements 26 can be carried by an endoprosthesis 70, such as an expanding stent or stent-graft, here shown on a support such as a balloon catheter or a catheter shaft 72. As shown, pads 28 with cutting elements 26 are mounted on the struts of stent 70. During expansion, cutting elements 26 can cut a calcified region, which can reduce the amount of force used to expand stent 70. In general, the stent can be of any desired shape and size (e.g., coronary stents, aortic stents, peripheral stents, gastrointestinal stents, urological stents, and neurological stents). In certain embodiments, a coronary stent can have an expanded diameter of from about two millimeters to about six millimeters. In some embodiments, a peripheral stent can have an expanded diameter of from about five millimeters to about 24 millimeters. In certain embodiments, a gastrointestinal and/or urological stent can have an expanded diameter of from about six millimeters to about 30 millimeters. In some embodiments, a neurological stent can have an expanded diameter of from about two millimeters to about 12 millimeters. The stent can be balloon-expandable, self-expandable, or a combination of both. The stent can be delivered and expanded according to conventional methods. Suitable catheter systems are described in, for example, Wang U.S. Pat. No. 5,195,969, and Hamlin U.S. Pat. No. 5,270,086. Suitable stents and stent delivery systems are also exemplified by the NIR on Ranger® system, available from Boston Scientific Scimed, Maple Grove, Minn. Other methods of carrying and delivering an endoprosthesis is described in U.S. Ser. No. 10/283,815, filed Oct. 30, 2002 and entitled "Medical Devices With Magnetic Powered Actuation."

All publications, references, applications, and patents referenced in this application are herein incorporated by reference in their entirety.

Other embodiments are in the claims.

What is claimed is:

1. A system, comprising:
an inflatable balloon secured to a catheter shaft;
a mounting pad secured to the inflatable balloon, the mounting pad comprising:
a polymeric material; and
a plurality of fibers dispersed within the polymeric material, wherein the fibers are substantially oriented along a longitudinal direction of the mounting pad; and
a scoring element attached to the mounting pad,
wherein an elongation at break of the mounting pad is at least about two times less than an elongation at break of the polymeric material.

2. The system of claim 1, wherein the elongation at break of the mounting pad is at least about five times less than the elongation at break of the polymeric material.

3. The system of claim 1, wherein the elongation at break of the mounting pad is at least about 10 times less than the elongation at break of the polymeric material.

4. The system of claim 1, wherein the elongation at break of the mounting pad is at least about 100 times less than the elongation at break of the polymeric material.

5. The system of claim 1, wherein the mounting pad has a percentage of elongation at break of at least about 50%.

6. The system of claim 1, wherein the polymeric material is selected from the group consisting of urethanes, silicones, natural rubbers, elastomers and combinations thereof.

7. The system of claim 1, wherein the fibers are selected from the group consisting of silk fibers, boron fibers, carbon fibers, polymer fibers, glass fibers, ceramic fibers and combinations thereof.

8. The system of claim 7, wherein the fibers have an average aspect ratio of at least about 10 to 1.

9. The system of claim 1, wherein the mounting pad has a longitudinal axis, and at least about 50% of the fibers are oriented within about 30° of the longitudinal axis of the mounting pad.

10. The system of claim 1, wherein the plurality of fibers comprises less than about 10% of the weight of the mounting pad.

11. The system of claim 1, wherein the inflatable balloon has a diameter of at least about 1.5 millimeters when inflated.

12. The system of claim 1, wherein a tensile strength of the mounting pad is at least about two times greater than a tensile strength of the polymeric material.

13. A system, comprising:
an inflatable balloon secured to a catheter shaft;
a mounting pad secured to the inflatable balloon, the mounting pad comprising:
a polymeric material; and
a plurality of fibers dispersed within the polymeric material, wherein the fibers are substantially oriented along a longitudinal direction of the mounting pad; and
a scoring element attached to the mounting pad,
wherein a tensile strength of the mounting pad is at least about two times greater than a tensile strength of the polymeric material.

14. The system of claim 13, wherein the tensile strength of the mounting pad is at least about 10 times greater than the tensile strength of the polymeric material.

15. The system of claim 13, wherein the tensile strength of the mounting pad is at least about 50 times greater than the tensile strength of the polymeric material.

16. The system of claim 13, wherein tensile strength of the mounting pad is at least about 3,000 psi.

17. The system of claim 13, wherein the polymeric material is selected from the group consisting of urethanes, silicones, natural rubbers, elastomers and combinations thereof.

18. The system of claim 13, wherein the fibers are selected from the group consisting of silk fibers, boron fibers, carbon fibers, polymer fibers, glass fibers, ceramic fibers and combinations thereof.

19. The system of claim 18, wherein the fibers have an average aspect ratio of at least about 10 to 1.

20. The system of claim 13, wherein the mounting pad has a longitudinal axis, and at least about 50% of the fibers are oriented within about 30° of the longitudinal axis of the mounting pad.

21. The system of claim 13, wherein the plurality of fibers comprises less than about 10% of the weight of the mounting pad.

22. The system of claim 21, wherein the inflatable balloon has a diameter of at least about 1.5 millimeters when inflated.

23. A system, comprising:
an inflatable balloon secured to a distal portion of a catheter shaft, the inflatable balloon having a longitudinal axis; and
a cutting element mounted to the inflatable balloon with a mounting pad attached between the cutting element and the inflatable balloon such that a longitudinal axis of the mounting pad is parallel to the longitudinal axis of the inflatable balloon, the mounting pad comprising:
a polymeric material; and
a plurality of fibers mixed in the polymeric material prior to forming the mounting pad, the plurality of fibers oriented in the polymeric material such that at least about 50% of the fibers are oriented within about 30° of the longitudinal axis of the mounting pad,
wherein an elongation at break of the mounting pad is at least about two times less than an elongation at break of the polymeric material.

24. The system of claim 23, wherein the elongation at break of the mounting pad is at least about five times less than the elongation at break of the polymeric material.

25. The system of claim 23, wherein the mounting pad has a percentage of elongation at break of at least about 50%.

26. The system of claim 23, wherein the inflatable balloon has a diameter of at least about 1.5 millimeters when inflated.

27. The system of claim 23, further comprising a plurality of mounting pads carried by the inflatable balloon, each of the plurality of mounting pads comprising a polymeric material and a plurality of fibers mixed in the polymeric material prior to forming the mounting pads, the plurality of fibers oriented in the polymeric material such that at least about 50% of the fibers are oriented within about 30° of the longitudinal axes of the mounting pads,
wherein, for each of the plurality of mounting pads, an elongation at break of the mounting pad is at least about two times less than an elongation at break of the polymeric material.

28. The system of claim 23, wherein the polymeric material is selected from the group consisting of urethanes, silicones, natural rubbers, elastomers and combinations thereof.

29. The system of claim 23, wherein the fibers are selected from the group consisting of silk fibers, boron fibers, carbon fibers, polymer fibers, glass fibers, ceramic fibers and combinations thereof.

30. The system of claim 29, wherein the fibers have an average aspect ratio of at least about 10 to 1.

31. The system of claim 23, wherein the plurality of fibers comprises less than about 10% of the weight of the mounting pad.

32. The system of claim 23, further comprising a bonding material between the mounting pad and the inflatable balloon.

33. A system, comprising:
an inflatable balloon secured to a distal portion of a catheter shaft, the inflatable balloon having a longitudinal axis; and
a cutting element mounted to the inflatable balloon with a mounting pad attached between the cutting element and the inflatable balloon such that a longitudinal axis of the mounting pad is parallel to the longitudinal axis of the inflatable balloon, the mounting pad comprising:
a polymeric material; and
a plurality of fibers mixed in the polymeric material prior to forming the mounting pad, the plurality of fibers oriented in the polymeric material such that at least about 50% of the fibers are oriented within about 30° of the longitudinal axis of the mounting pad,
wherein a tensile strength of the mounting pad is at least about two times greater than a tensile strength of the polymeric material.

34. The system of claim 33, wherein the tensile strength of the mounting pad is at least about 3,000 psi.

35. The system of claim 33, wherein the inflatable balloon has a diameter of at least about 1.5 millimeters when inflated.

36. The system of claim 33, further comprising a plurality a plurality of mounting pads carried by the inflatable balloon, each of the plurality of mounting pads comprising a polymeric material and a plurality of fibers mixed in the polymeric material prior to forming the mounting pads, the plurality of fibers oriented in the polymeric material such that at least about 50% of the fibers are oriented within about 30° of the longitudinal axes of the mounting pads,
wherein, for each of the plurality of mounting pads, a tensile strength of the mounting pad is at least about two times greater than a tensile strength of the polymeric material.

37. The system of claim 33, wherein the polymeric material is selected from the group consisting of urethanes, silicones, natural rubbers, elastomers and combinations thereof.

38. The system of claim 33, wherein the fibers are selected from the group consisting of silk fibers, boron fibers, carbon fibers, polymer fibers, glass fibers, ceramic fibers and combinations thereof.

39. The system of claim 38, wherein the fibers have an average aspect ratio of at least about 10 to 1.

40. The system of claim 33, wherein the plurality of fibers comprises less than about 10% of the weight of the mounting pad.

41. The system of claim 33, further comprising a bonding material between the mounting pad and the inflatable balloon.

42. A system, comprising:
an inflatable balloon secured to a catheter shaft;
a pad bonded to the inflatable balloon such that a longitudinal axis of the pad is parallel to a longitudinal axis of the inflatable balloon, the pad comprised of a polymeric material and a plurality of fibers mixed into the polymeric material of the pad such that the fibers are substantially oriented along the longitudinal axis of the pad; and
a scoring element attached to the pad,
wherein an elongation at break of the pad is at least about two times less than an elongation at break of the polymeric material; and
wherein the orientation of the plurality of fibers in the pad is such that the fibers increase the stiffness of the pad along the longitudinal axis of the pad but have little or no effect on the flexibility of the pad in directions transverse to the longitudinal axis of the pad.

43. The system of claim 42, wherein the elongation of break of the pad is at least about five times less than the elongation at break of the polymeric material.

44. The system of claim 42, wherein the inflatable balloon has a diameter of at least about 1.5 millimeters when inflated.

45. A system, comprising:
an inflatable balloon secured to a catheter shaft;
a pad bonded to the inflatable balloon such that a longitudinal axis of the pad is parallel to a longitudinal axis of the inflatable balloon, the pad comprising a polymeric material and a plurality of fibers mixed into the polymeric material of the pad such that the fibers are substantially oriented along the longitudinal axis of the pad; and
a scoring element attached to the pad,
wherein a tensile strength of the pad is at least about two times greater than a tensile strength of the polymeric material; and
wherein the orientation of the plurality of fibers in the pad is such that the fibers increase the stiffness of the pad along the longitudinal axis of the pad but have little or no effect on the flexibility of the pad in directions transverse to the longitudinal axis of the pad.

46. The system of claim 45, wherein the inflatable balloon has a diameter of at least about 1.5 millimeters when inflated.

47. A system, comprising:
   an inflatable balloon secured to a catheter shaft;
   a mounting pad having a surface, the mounting pad formed by combining a plurality of fibers with a polymer precursor of one or monomers and one or more activators in a molten state, mixing the polymer precursor and the plurality of fibers together to disperse the plurality of fibers throughout the polymer precursor, passing the polymer precursor with the plurality of fibers dispersed therein through an orifice to orient the plurality of fibers such that at least 50% of the fibers are oriented within about 30 degrees of a longitudinal direction of the mounting pad, and then curing the polymer precursor with the oriented fibers dispersed therein;
   a cutting element attached to the mounting pad; and
   a bonding material on the surface of the mounting pad bonding the mounting pad to the inflatable balloon,
   wherein an elongation at break of the mounting pad is at least about two times less than an elongation at break of the polymeric material.

48. The system of claim 47, wherein the bonding material is selected from the group consisting of polyurethanes, adhesives, cyanoacrylates and combinations thereof.

49. A system, comprising:
   an inflatable balloon secured to a catheter shaft;
   a mounting pad having a surface, the mounting pad formed by combining a plurality of fibers with a polymer precursor of one or monomers and one or more activators in a molten state, mixing the polymer precursor and the plurality of fibers together to disperse the plurality of fibers throughout the polymer precursor, passing the polymer precursor with the plurality of fibers dispersed therein through an orifice to orient the plurality of fibers such that at least 50% of the fibers are oriented within about 30 degrees of a longitudinal direction of the mounting pad, and then curing the polymer precursor with the oriented fibers dispersed therein;
   a cutting element attached to the mounting pad; and
   a bonding material on the surface of the mounting pad bonding the mounting pad to the inflatable balloon,
   wherein a tensile strength of the mounting pad is at least about two times greater than a tensile strength of the polymeric material.

50. The system of claim 49, wherein the bonding material is selected from the group consisting of polyurethanes, adhesives, cyanoacrylates and combinations thereof.

* * * * *